(12) United States Patent
Wolman et al.

(10) Patent No.: US 12,042,646 B2
(45) Date of Patent: *Jul. 23, 2024

(54) HEART RATE MEASUREMENT USING BLOOD PUMP IMPELLER LOCATION

(71) Applicant: HeartWare, Inc., Miami Lakes, FL (US)

(72) Inventors: Justin Wolman, Aventura, FL (US); Fernando Casas, Miami Lakes, FL (US); Carlos Reyes, Davie, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/654,724

(22) Filed: Mar. 14, 2022

(65) Prior Publication Data
US 2022/0203083 A1 Jun. 30, 2022

Related U.S. Application Data

(63) Continuation of application No. 16/221,768, filed on Dec. 17, 2018, now Pat. No. 11,273,299.
(Continued)

(51) Int. Cl.
*A61M 60/148* (2021.01)
*A61M 60/178* (2021.01)
(Continued)

(52) U.S. Cl.
CPC ........ *A61M 60/148* (2021.01); *A61M 60/178* (2021.01); *A61M 60/216* (2021.01);
(Continued)

(58) Field of Classification Search
CPC ........ A61M 2205/3334; A61M 60/205; A61M 60/50; A61M 60/422; A61M 60/148;
(Continued)

(56) References Cited

U.S. PATENT DOCUMENTS

| 5,888,242 A | 3/1999 | Antaki et al. |
| 7,645,225 B2 | 1/2010 | Medvedev et al. |

(Continued)

FOREIGN PATENT DOCUMENTS

| CN | 101202614 A | 6/2008 |
| CN | 105825071 A | 8/2016 |

(Continued)

OTHER PUBLICATIONS

Communication pursuant to Article 94(3) EPC from counterpart European Application No. 18830655.9 dated Apr. 12, 2022, 5 pp.
(Continued)

*Primary Examiner* — Lynsey C Eiseman
*Assistant Examiner* — Amanda L Steinberg
(74) *Attorney, Agent, or Firm* — Shumaker & Sieffert, P.A.

(57) ABSTRACT

A method of determining a heart rate of a patient having an implanted blood pump including applying a voltage to a plurality of coils of a stator of the blood pump to produce an electromagnetic force to rotate a rotor in communication with the plurality of coils; displaying a waveform associated with a back electromotive force in the plurality of coils of the blood pump, the waveform being proportional to an axial position of the rotor relative to the stator; determining a time interval between a first alteration in the waveform relative to a baseline and a second alteration in the waveform relative to the baseline; and determining the heart rate of the patient based on the time interval.

20 Claims, 5 Drawing Sheets

Related U.S. Application Data

(60) Provisional application No. 62/607,478, filed on Dec. 19, 2017.

(51) Int. Cl.
*A61M 60/216* (2021.01)
*A61M 60/422* (2021.01)
*A61M 60/515* (2021.01)
*A61M 60/538* (2021.01)
*A61M 60/857* (2021.01)

(52) U.S. Cl.
CPC ........ *A61M 60/422* (2021.01); *A61M 60/515* (2021.01); *A61M 60/538* (2021.01); *A61M 60/857* (2021.01); *A61M 2205/3334* (2013.01)

(58) Field of Classification Search
CPC .............. A61M 60/122; A61M 60/178; A61M 60/857; A61M 60/515; A61M 60/216
See application file for complete search history.

(56) References Cited

U.S. PATENT DOCUMENTS

| | | |
|---|---|---|
| 7,983,368 B2 | 7/2011 | Cranford, Jr. et al. |
| 8,007,254 B2 | 8/2011 | LaRose et al. |
| 8,961,390 B2 | 2/2015 | LaRose et al. |
| 9,561,313 B2 | 2/2017 | Taskin |
| 10,001,419 B2 | 6/2018 | Kolbenschlag et al. |
| 10,033,319 B2 | 7/2018 | Da Silva et al. |
| 10,610,627 B2 | 4/2020 | Hayward |
| 11,273,299 B2 | 3/2022 | Wolman et al. |
| 2004/0215050 A1 | 10/2004 | Morello |
| 2016/0166211 A1 | 6/2016 | Brown et al. |
| 2018/0078159 A1 | 3/2018 | Edelman et al. |
| 2019/0030230 A1 | 1/2019 | Connor |

FOREIGN PATENT DOCUMENTS

| | | |
|---|---|---|
| CN | 106039441 A | 10/2016 |
| CN | 205691271 U | 11/2016 |
| CN | 106712646 A | 5/2017 |
| CN | 106999069 A | 8/2017 |
| WO | 2011163421 A1 | 12/2011 |
| WO | 2018026769 A1 | 2/2018 |
| WO | 2018057732 A1 | 3/2018 |

OTHER PUBLICATIONS

International Preliminary Report on Patentability from International Application No. PCT/US2018/065936, dated Jun. 23, 2020, 7 pp.
International Search Report and Written Opinion of International Application No. PCT/US2018/065936, dated Mar. 27, 2019, 12 pp.
Prosecution History from U.S. Appl. No. 16/221,768, dated Apr. 2, 2021 through Nov. 8, 2021, 26 pp.
First Office Action and Search Report, and translation thereof, from counterpart Chinese Application No. 201880081949.5, dated Nov. 30, 2022, 17 pp.

HEART RATE MEASUREMENT USING BLOOD PUMP IMPELLER LOCATION

CROSS-REFERENCE TO RELATED APPLICATION

This application is a continuation of U.S. application Ser. No. 16/221,768, filed Dec. 17, 2018, which claims the benefit of U.S. Application Ser. No. 62/607,478, filed Dec. 19, 2017, each of which is incorporated by reference in its entirety.

FIELD

The present technology is generally related to determining heart rate measurements of patients having an implanted blood pump.

BACKGROUND

Mechanical Circulatory Support Devices ("MCSDs") are commonly used to assist the pumping action of a failing heart. Typically, an MCSD includes an implantable blood pump that is surgically implanted in a patient's body. The MCSD may include a housing with an inlet, an outlet, and a rotor mounted therein. The inlet is connected to a chamber of the patient's heart, typically the left ventricle, whereas the outlet is connected to an artery, such as the aorta. Rotation of the rotor drives blood from the inlet towards the outlet and thus assists blood flow from the chamber of the heart into the artery. One exemplary MCSD is the MVAD® Pump. The MVAD® Pump is further discussed in U.S. Pat. Nos. 8,007,254 and 9,561,313, the disclosures of which are incorporated herein in the entirety. Unfortunately, determining a heart rate of a patient having an operating MCSD implanted within the patient's body may be difficult, particularly when there is a non-linear relationship between a blood flow rate through the blood pump and a motor current of the blood pump.

SUMMARY

The techniques of this disclosure generally relate to determining a heart rate of a patient having an implanted blood pump during operation of the blood pump.

In one aspect, the present disclosure provides a method of determining a heart rate of a patient having an implanted blood pump including applying a voltage to a plurality of coils of a stator of the blood pump to produce an electromagnetic force to rotate a rotor in communication with the plurality of coils; displaying a waveform associated with a back electromotive force in the plurality of coils of the blood pump, the waveform being proportional to an axial position of the rotor relative to the stator; determining a time interval between a first alteration in the waveform relative to a baseline and a second alteration in the waveform relative to the baseline; and determining the heart rate of the patient based on the determined time interval.

In another aspect, the disclosure provides the first alteration being a first rise in the waveform relative to the baseline and the second alteration being a second rise in the waveform relative to the baseline.

In another aspect, the disclosure provides recording one or more-time intervals between one or more rises in the waveform relative to the baseline and calculating the heart rate based on the time intervals.

In another aspect, the disclosure provides the baseline being an upper hysteresis band.

In another aspect, the disclosure provides the first alteration being a first fall in the waveform relative to the baseline and the second alteration being a second fall in the waveform relative to the baseline.

In another aspect, the disclosure provides recording one or more-time intervals between one or more falls in the waveform relative to the baseline and calculating the heart rate based on the one or more-time intervals.

In another aspect, the disclosure provides the axial position of the rotor relative to the stator being proportional to a thrust through the blood pump, and the thrust is proportional to a fluid flow through the blood pump.

In another aspect, the disclosure provides determining the heart rate of the patient in a presence of a non-linear relationship between the fluid flow through the blood pump and a motor voltage of the blood pump.

In one aspect, the present disclosure provides a method of determining a heart rate of a patient having an implanted blood pump including generating a waveform representing a back electromotive force in one or more coils of the blood pump during operation; detecting one or more alterations in the waveform relative to a baseline, the alterations being one of the group consisting of a rise and a fall in the waveform relative to the baseline; recording a time interval between at least a pair of adjacent alterations of the alterations; and determining the heart rate of the patient based on the time interval.

In another aspect, the disclosure provides the blood pump including a rotor and a stator in communication with the rotor, and the waveform is proportional to an axial position of the rotor relative to the stator.

In another aspect, the disclosure provides the axial position of the rotor relative to the stator being proportional to a thrust through the blood pump, and the thrust is proportional to a fluid flow through the blood pump.

In another aspect, the disclosure provides determining the heart rate of the patient in a presence of a non-linear relationship between the fluid flow through the blood pump and a motor current of the blood pump.

In another aspect, the disclosure provides the time interval corresponding to a complete heartbeat of the patient.

In another aspect, the disclosure provides including correlating the time interval to a predetermined figure.

In another aspect, the disclosure provides dividing the time interval by the predetermined figure of sixty to determine a number of heart beats per minute.

In another aspect, the disclosure provides the baseline being an upper hysteresis band, and the rise in the waveform includes a crossing of the upper hysteresis band.

In another aspect, the disclosure provides correlating the waveform to a lower hysteresis band separate from the upper hysteresis band, and wherein the fall in the waveform includes a crossing of the lower hysteresis band.

In another aspect, the disclosure provides calculating the heart rate of the patient based on a frequency analysis of the waveform.

In another aspect, the disclosure provides determining a variability with respect to the determined heart rate of the patient over a select duration.

In one aspect, the present disclosure provides a system for determining a heart rate of a patient including a control circuit in communication with an implantable blood pump including a rotor and a stator in communication with the rotor, the control circuit including control circuitry configured to generate a waveform representing a back electromotive force in a plurality of coils of the blood pump during operation, the waveform being proportional to an axial position of the rotor relative to the stator; detect a plurality of alterations in the waveform relative to a baseline, the plurality of alterations being one of the group consisting of a rise and a fall in the waveform relative to the baseline; record a plurality of time intervals between adjacent alterations of the plurality of alterations, each of the plurality of time intervals corresponding to a complete heartbeat of the patient; correlate each of the plurality of time intervals to a predetermined figure; and determine the heart rate of the patient based on the correlated plurality of time intervals.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
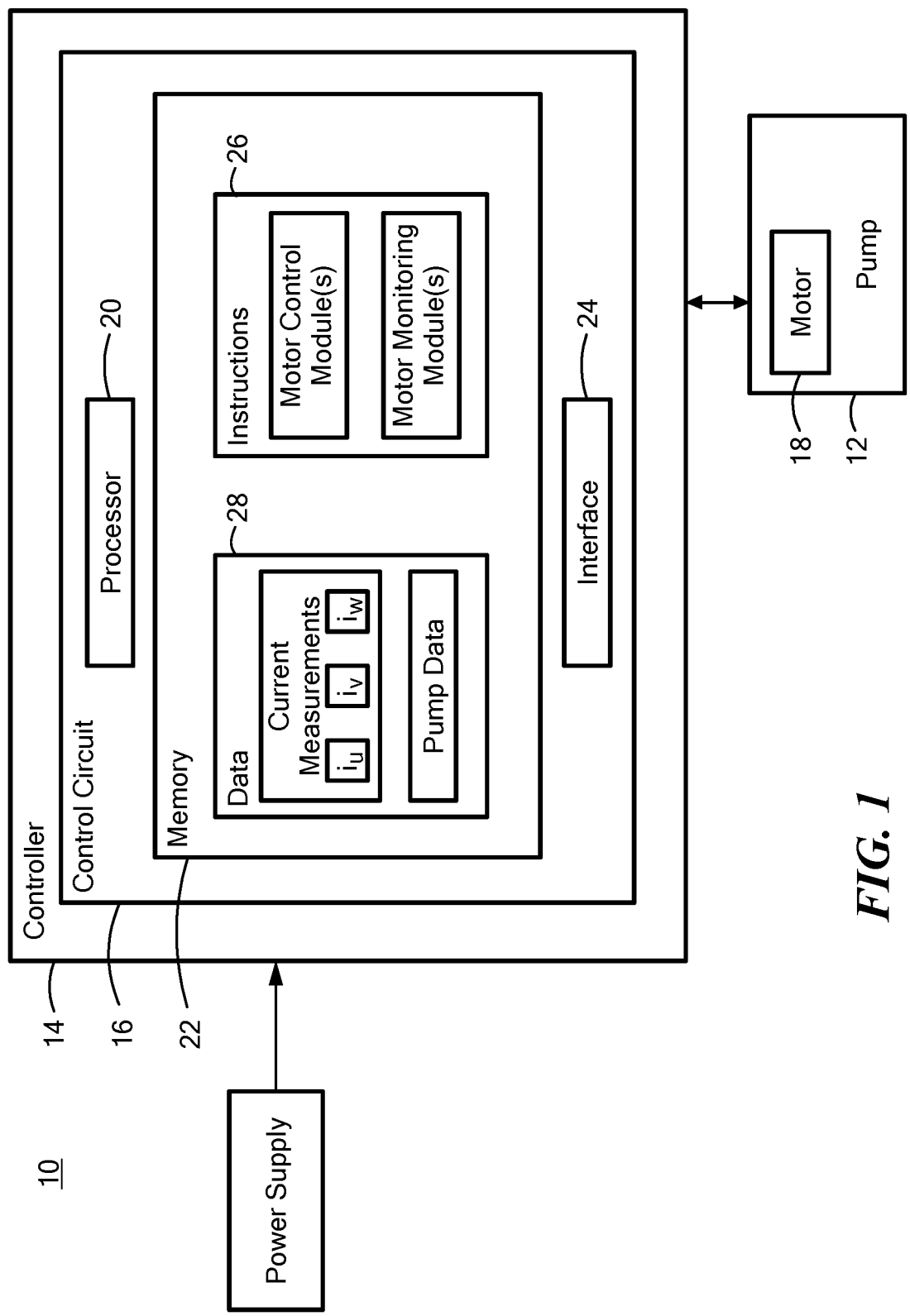
FIG. 1 is a block diagram that illustrates a system including an implantable blood pump and a controller including a processor in communication with the blood pump.

Before describing in detail exemplary embodiments, it is noted that the embodiments reside primarily in combinations of system components and processing steps related to a method and system for determining a heart rate of a patient having an implanted blood pump. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawings in which like reference designators refer to like elements there is shown in FIG. 1 a block diagram of an exemplary system 10 constructed in accordance with the principles of the present application and designated generally "10." The system 10 includes an implantable blood pump 12 in communication with a controller 14. The blood pump 12 may be the MVAD® Pump or another mechanical circulatory support device fully or partially implanted within the patient. The controller 14 includes a control circuit 16 having control circuitry for monitoring and controlling startup and subsequent operation of a motor 18 implanted within the blood pump 12. The controller 14 may also include a processor 20 having processing circuitry, a memory 22, and an interface 24. The memory 22 stores information accessible by the processor 20 and processing circuitry, including instructions 26 executable by the processor 20 and/or data 28 that may be retrieved, manipulated, and/or stored by the processor 20.

The blood pump 12 may be a continuous flow blood pump, such as, without limitation, the MVAD® Pump referenced above, and may include a housing having a rotor therein. The system 10 and the blood pump 12 may be used in conjunction with a method of determining a heart rate of a patient having the blood pump implanted with the patient's body based upon an axial position of the rotor with respect to the housing, as discussed in further detail below.

Figure 2:
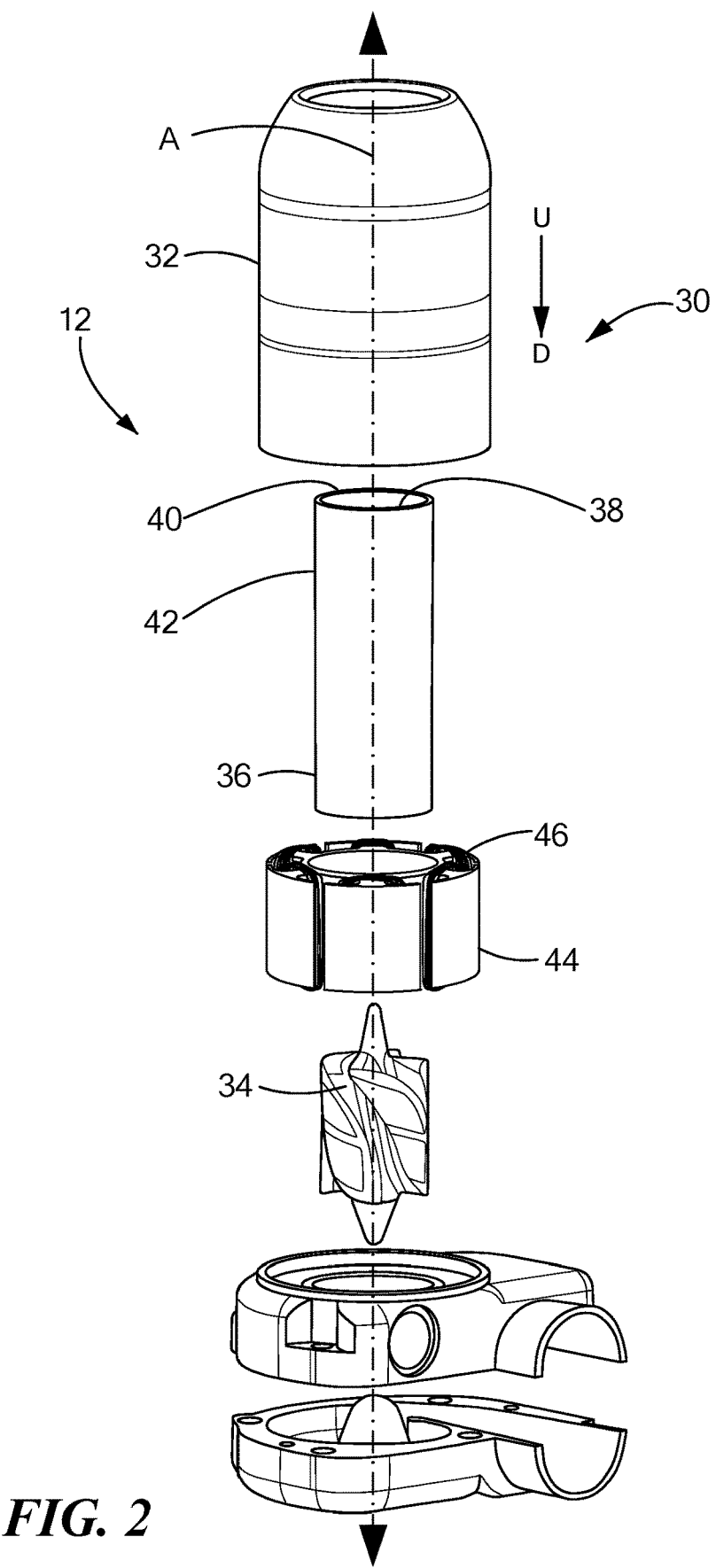
FIG. 2 is an exploded view that illustrates an exemplary blood pump constructed in accordance of the principles of the present application.

FIG. 2 is an exploded view of the blood pump 12 include a housing 30 having an inlet cannula 32 and a rotor 34 such as an impeller, proximate the inlet cannula 32 to impel the blood. The inlet cannula 32 includes an inner tube 36 formed from a non-magnetic material, such as a ceramic. The inner tube 36 includes an interior surface 38 defining a cylindrical bore 40 for receiving the rotor 34 therein. The inner tube 36 also includes a cylindrical outer surface 42 surrounded by a stator 44 having one or more coils 46. A voltage is applied to the coils 46 from a drive circuit (not shown) to produce an electromagnetic force to rotate the rotor 34. In particular, the electromagnetic force of the coils 46 exhibits an electromagnetic field which interacts with a magnetic field of the rotor 34 to suspend the rotor 34 within the cylindrical bore 40 and rotate the rotor 34. In addition to or in lieu of the magnetic forces, the rotor 34 may be suspended within the housing 30 using one or more hydrodynamic forces.

Rotation of the rotor 34 impels the blood along a fluid flow path from an upstream direction U to a downstream direction D through the inner tube 36. The fluid flow path may be referred to as a blood flow path. Further details associated with rotary blood pumps are described in U.S. Pat. No. 8,007,254, the disclosure of which is incorporated herein by reference in the entirety. The blood pump 12 defines a housing axis "A" extending therethrough and along the fluid flow path from the upstream to the downstream direction. The rotor 34 moves in an axial direction relative to the housing 30 along the housing axis. When fluid, such as blood, passes through the blood pump 12, the fluid imparts a thrust on the rotor 34 which causes the rotor 34 to move. A magnitude of the thrust is related to the fluid flow rate through the blood pump 12. In other words, the axial position of the rotor 34 relative to the housing 30 is proportional to the fluid flow rate through the blood pump 12, which is proportional to the thrust.

The patient's heart beat is determined by analyzing the axial position of the rotor 34 relative to the housing 30, and particularly the stator 44. For example, a back electromotive force ("BEMF") is produced in the coils 46 when the voltage is applied to the coils 46 to rotate the rotor 34. In other words, the BEMF is the voltage induced in the coils 46 by rotating the rotor 34. The axial movement of the rotor 34 alters the alignment between the rotor 34 and the coils 46 which alters the BEMF. The slope of the BEMF is analyzed to derive the patient's heart beat. In addition to or in lieu of using the BEMF, a sensor (not shown) disposed within the housing 30 may be used to determine the axial position of the rotor 34 relative to the stator 44.

Figure 3:
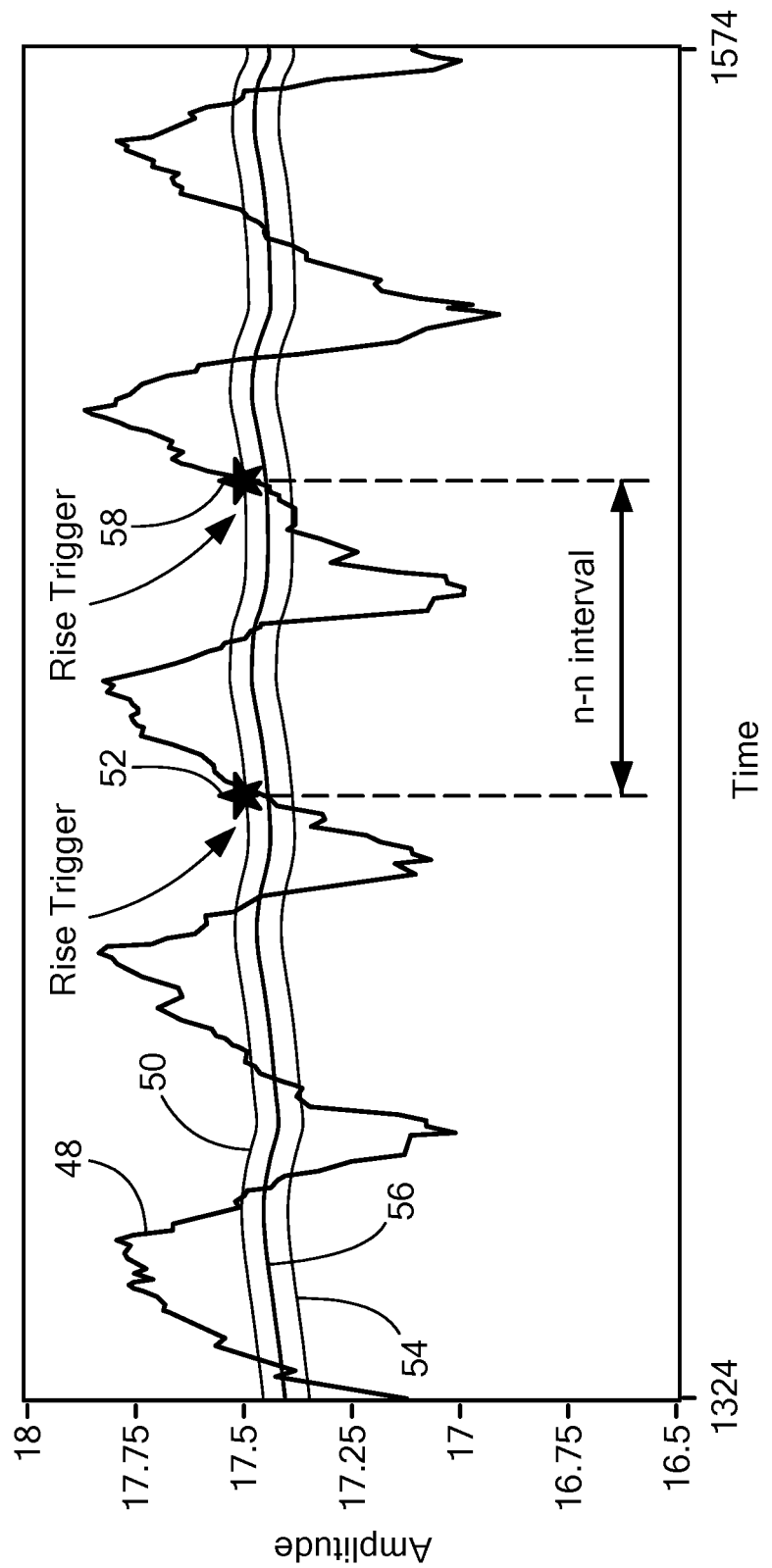
FIG. 3 is a graph that illustrates a waveform associated with a back electromotive force in one or more coils of a rotor of the blood pump shown in FIG. 1.

FIG. 3 is a graph that illustrates an exemplary waveform 48 of the BEMF in a pulsatile flow system over approximately ten seconds at sixty beats per minute. The term approximately includes a deviation within plus or minus five seconds. The control circuit 16 and the control circuitry (FIG. 1) are configured to generate the waveform 48. The waveform 48 shows alterations in the BEMF signal's amplitude relative to a baseline 50 over time. The alterations in the waveform 48 are detected and viewed and/or recorded to determine the patient's heart beat. For example, a time interval between adjacent pairs of rises and/or falls in the waveform 48 relative to the baseline 50 represent a duration of an individual heartbeat. In other words, the time interval is the time it takes to complete a single complete heartbeat. The heartbeat is correlated to a predetermined figure to determine the patient's heart rate in beats per minute. For example, the predetermined figure may be the number 60 with the time interval being divided by the number 60 to output the heart rate in beats per minute. The number of time intervals used to determine the heart rate may vary. The heart rate may be determined regardless of a speed of the blood pump 12, such as when there is a non-linear relationship between the fluid flow through the blood pump 12 and the speed, which may occur in the MVAD® Pump.

In another configuration, the heart rate may be determined by performing a frequency analysis of the waveform 48. The time interval calculations and/or the frequency analysis are performed using one or more algorithms or other calculation methods. The waveform 48 may be displayed on a monitor of the controller 14 or a remote location, such as a remote location viewable by a clinician. The waveform 48 is provided for illustrative purposes as the duration and number of beats per minute may vary in accordance with individual patients. The determined heart rate may be used to derive additional parameters, such as the patient's heart rate variability over time, for clinical or other use. For example, the variability with respect to the patient's heart rate may be determined over weeks, months, and/or years to determine whether the patient's health condition is deteriorating.

FIG. 3 depicts a first alteration in the waveform 48 as a first rise 52 in the waveform 48 relative to the baseline 50. The baseline 50 is an upper hysteresis band which is separate from a lower hysteresis band 54 by a filter 56. The baseline 50 or the upper hysteresis band and the lower hysteresis band 54 are used to reduce the occurrence of faulty triggers in the rises, which may otherwise occur due to outside factors, such as noise. The rise in the waveform 48 refers to the waveform 48 crossing the baseline 50. Once the first rise 52 is detected, a timer runs until a second rise 58 in the waveform 48 is detected relative to the baseline 50 and the timer stops. A time interval, designated as an "n-n interval", is recorded between the first rise 52 and the second rise 58 and stored in the memory 22 (FIG. 1). The time interval between the first rise 52 and the second rise 58 represents the time duration between individual heart beats.

Figure 4:
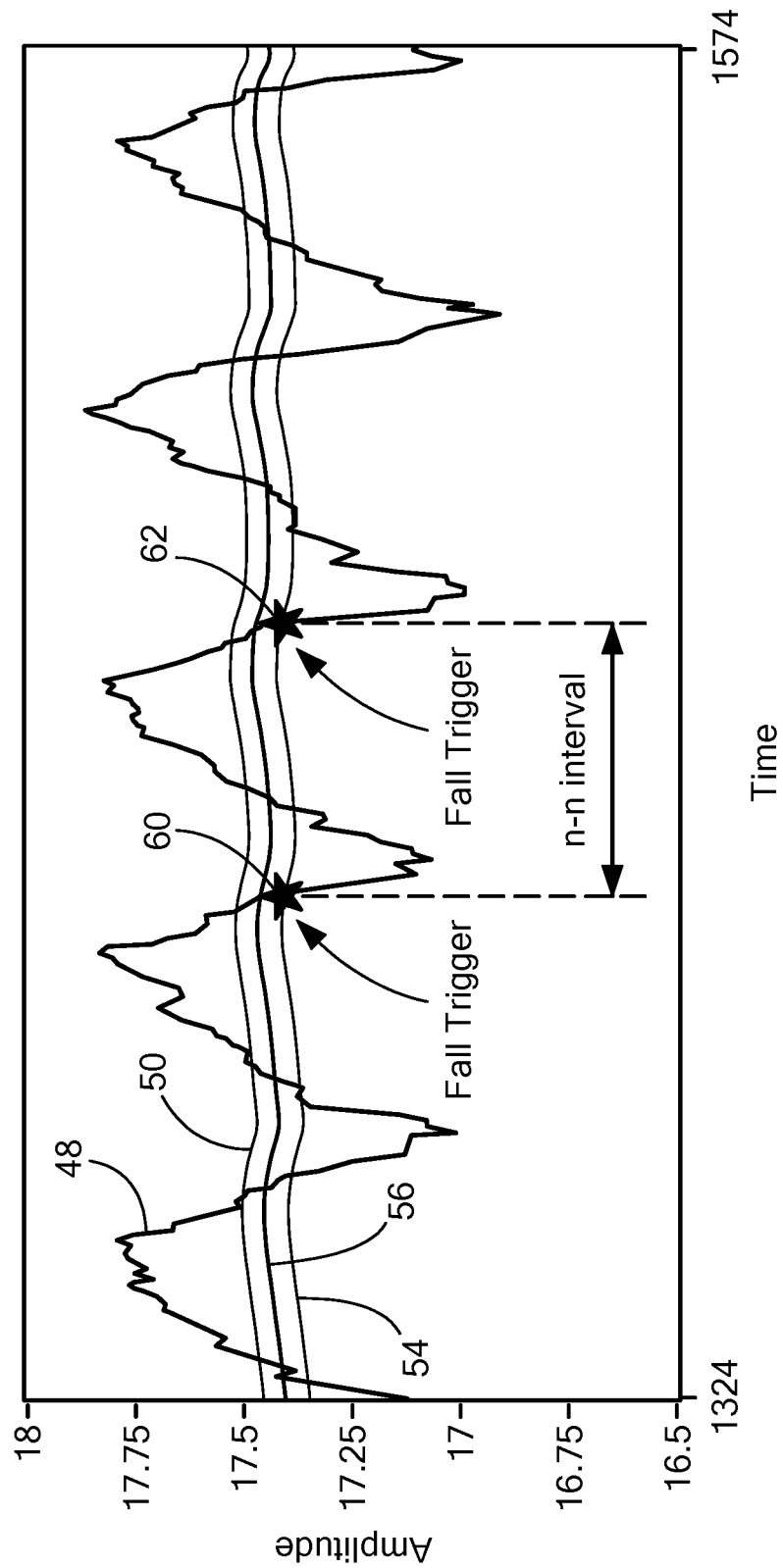
FIG. 4 is another graph that illustrates the waveform associated with the back electromotive force in one or more coils of the rotor of the blood pump shown in FIG. 1.

FIG. 4 is a graph that illustrates a first alteration of the waveform 48 as a first fall 60 in the waveform 48 relative to the baseline 50. The fall in the waveform 48 refers to the waveform 48 crossing the lower hysteresis band 54. Similar to the first rise 52 in the waveform 48 (FIG. 3), when the first fall 60 is detected a timer runs until a second fall 62 in the waveform 48 is detected relative to the baseline 50, at which time the timer stops. A time interval between the first fall 60 and the second fall 62, such as the n-n interval, is recorded and stored in the memory 22. Two or more of the time intervals may be determined and recorded to determine the average heart rate.

Figure 5:
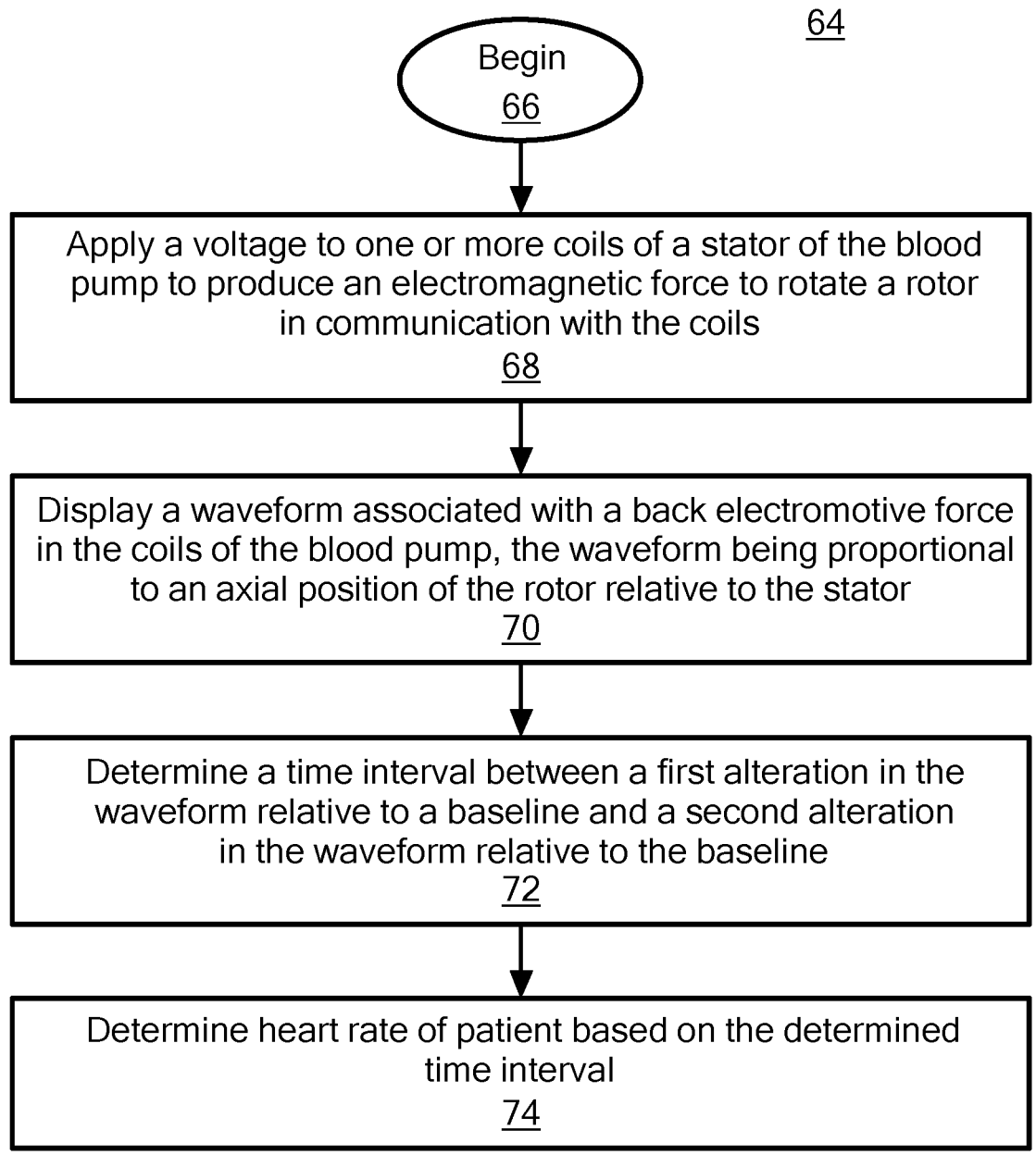
FIG. 5 is a flow diagram that illustrates a method of determining a heart rate of a patient having the blood pump implanted in the patient during operation of the blood pump.

FIG. 5 is a flow chart depicting steps of an exemplary method 64 of determining the heart rate of a patient having an implanted blood pump. The control circuit 16 and the control circuitry (FIG. 1) may be configured to execute the steps of the method. In one exemplary configuration, the method begins with step 66 and proceeds to step 68 of applying a voltage to the coils 28 of the stator 44 of the blood pump 12 to produce an electromagnetic force to rotate the rotor 34 in communication with the coils 28. As mentioned above, the voltage is applied through a drive circuit (not shown). At step 70, the method includes displaying the waveform 48 associated with the back electromotive force in the coils 28 of the blood pump 12 with the waveform 48 being proportional to an axial position of the rotor 34 relative to the stator 44. The waveform 48 may be generated using the controller 14 and control circuit 16 (FIG. 1) and displayed on a monitor of the controller 14 (not shown) or at another remote location. At step 72, the method 64 includes determining the time interval between the first alteration in the waveform 48 relative to the baseline 50 and a second alteration in the waveform 48 relative to the baseline 50. The first and second alterations are the rise and/or the fall with respect to the baseline 50. At step 74, the method 64 includes determining the heart rate of the patient based on the determined time interval as discussed in further detail above.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system comprising:
an implantable blood pump comprising a rotor and a stator with a plurality of coils, wherein the implantable blood pump is configured to pump blood from a chamber of a heart of a patient; and
a controller comprising a memory and processing circuitry configured to:
generate a waveform representing a back electromotive force in the plurality of coils during operation of the implantable blood pump;
detect a plurality of alterations in the waveform relative to a baseline, the plurality of alterations including one or both of rises and falls in the waveform relative to the baseline;
record a time interval between at least a pair of adjacent alterations of the plurality of alterations;
determine a heart rate of the patient based on the time interval; and
output an indication of the heart rate.

2. The system of claim 1, wherein the waveform is proportional to an axial position of the rotor relative to the stator.

3. The system of claim 2, wherein the axial position of the rotor relative to the stator is proportional to a thrust through the implantable blood pump, and the thrust is proportional to a fluid flow through the implantable blood pump.

4. The system of claim 1, wherein the processing circuitry is further configured to determine the heart rate of the patient in a presence of a non-linear relationship between a fluid flow through the implantable blood pump and a motor current of the implantable blood pump.

5. The system of claim 1, wherein the time interval corresponds to a complete heartbeat of the patient.

6. The system of claim 5, wherein the processing circuitry is further configured to correlate the time interval to a predetermined figure to determine a number of heart beats per minute.

7. The system of claim 1, wherein the baseline corresponds to an upper hysteresis band, and the processing circuitry is configured to detect a rise in the waveform in response to the waveform crossing the upper hysteresis band.

8. The system of claim 1, wherein the baseline corresponds to a lower hysteresis band, and the processing circuitry is configured to detect a fall in the waveform in response to the waveform crossing the lower hysteresis band.

9. The system of claim 1, wherein the processing circuitry is further configured to determine the heart rate of the patient based on a frequency analysis of the waveform.

10. The system of claim 1, wherein the processing circuitry is further configured to determine a variability with respect to the determined heart rate of the patient over a select duration.

11. A device comprising:
a memory; and
processing circuitry configured to:
generate a waveform representing a back electromotive force in a plurality of coils of a blood pump device during operation of the blood pump device;
detect a plurality of alterations in the waveform relative to a baseline, the plurality of alterations including one or both of rises and falls in the waveform relative to the baseline;
record a time interval between at least a pair of adjacent alterations of the plurality of alterations;
determine a heart rate of a patient based on the time interval; and
output an indication of the heart rate.

12. The device of claim 11, wherein the waveform is proportional to an axial position of a rotor of the blood pump device relative to a stator of the blood pump device.

13. The device of claim 11, wherein the processing circuitry is further configured to:
determine the heart rate of the patient in a presence of a non-linear relationship between a fluid flow through the blood pump device and a motor current of the blood pump device.

14. The device of claim 11, wherein the time interval corresponds to a complete heartbeat of the patient.

15. The device of claim 11, wherein the baseline corresponds to an upper hysteresis band, and the processing circuitry is configured to detect a rise in the waveform in response to the waveform crossing the upper hysteresis band.

16. The device of claim 11, wherein the baseline corresponds to a lower hysteresis band, and the processing circuitry is configured to detect a fall in the waveform in response to the waveform crossing the lower hysteresis band.

17. A method comprising:
generating a waveform representing a back electromotive force in a plurality of coils of a blood pump device during operation of the blood pump device;
detecting a plurality of alterations in the waveform relative to a baseline, the plurality of alterations including one or both of rises and falls in the waveform relative to the baseline;
recording a time interval between at least a pair of adjacent alterations of the plurality of alterations;
determining a heart rate of a patient based on the time interval; and
outputting an indication of the heart rate.

18. The method of claim 17, wherein the waveform is proportional to an axial position of a rotor of the blood pump device relative to a stator of the blood pump device.

19. The method of claim 17, further comprising determining the heart rate of the patient in a presence of a non-linear relationship between a fluid flow through the blood pump device and a motor current of the blood pump device.

20. The method of claim 17, wherein the time interval corresponds to a complete heartbeat of the patient.

* * * * *